(12) United States Patent
Gupta et al.

(10) Patent No.: US 10,345,210 B2
(45) Date of Patent: Jul. 9, 2019

(54) METHOD TO ESTIMATE STRAIN RATE DEPENDENT ELASTIC MODULUS OF MATERIALS USING DYNAMIC MECHANICAL ANALYSIS DATA

(71) Applicant: NEW YORK UNIVERSITY, New York, NY (US)

(72) Inventors: Nikhil Gupta, Ossining, NY (US); Steven E. Zeltmann, Brooklyn, NY (US)

(73) Assignee: NEW YORK UNIVERSITY, New York, NY (US)

( * ) Notice: Subject to any disclaimer, the term of this patent is extended or adjusted under 35 U.S.C. 154(b) by 81 days.

(21) Appl. No.: 15/676,873

(22) Filed: Aug. 14, 2017

(65) Prior Publication Data

US 2018/0045630 A1   Feb. 15, 2018

Related U.S. Application Data

(60) Provisional application No. 62/375,315, filed on Aug. 15, 2016.

(51) Int. Cl.
  *G01N 3/18*   (2006.01)
  *G01N 3/32*   (2006.01)
  *G01N 33/44*  (2006.01)

(52) U.S. Cl.
  CPC ............... *G01N 3/18* (2013.01); *G01N 3/32* (2013.01); *G01N 33/442* (2013.01); *G01N 2203/0005* (2013.01); *G01N 2203/0224* (2013.01); *G01N 2203/0226* (2013.01)

(58) Field of Classification Search
  CPC ........... G01N 3/18; G01N 3/32; G01N 33/442
  See application file for complete search history.

(56) References Cited

U.S. PATENT DOCUMENTS

2016/0046832 A1*  2/2016  Wroblesky ........... C09D 167/00
                                                    264/489

OTHER PUBLICATIONS

Perkinelmer, Inc., "Dynamic Mechanical Analysis (DMA)—A Beginner's Guide", 2008, 23 pages, PerkinElmer, Inc., Waltham, MA.
Zeltmann et al., "Prediction of strain rate sensitivity of high density polyethylene using integral transform of dynamic mechanical analysis data", Polymer, Sep. 28, 2016, 101:1-6.
Zeltmann et al., "Prediction of modulus at various strain rates from dynamic mechanical analysis data for polymer matrix composites", Composites Part B, Jul. 1, 2017, 120:27-34.
Koomson et al., "Strain rate sensitivity of polycarbonate and vinyl ester from dynamic mechanical analysis experiments", Advanced Composites Sciences, accepted 2017, pp. 1-9.

\* cited by examiner

*Primary Examiner* — Jamel E Williams
(74) *Attorney, Agent, or Firm* — Foley & Lardner LLP

(57) ABSTRACT

A method for predicting an elastic modulus of a material includes providing a sample in a dynamic mechanical analysis device, performing a temperature sweep test to obtain a first data set, performing a frequency sweep test to obtain a second data set, using the second data set to generate a master curve in a frequency domain of the at least one of the storage modulus of the sample or the loss modulus of the sample using time-temperature superposition, converting the master curve in the frequency domain into a time domain relaxation function, and using the time domain relaxation function to predict the elastic modulus of the material.

20 Claims, 16 Drawing Sheets

FIG. 1(a)
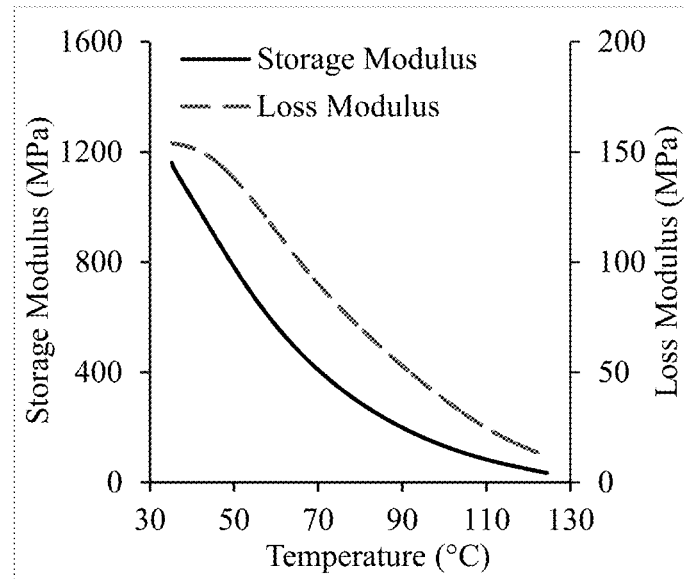
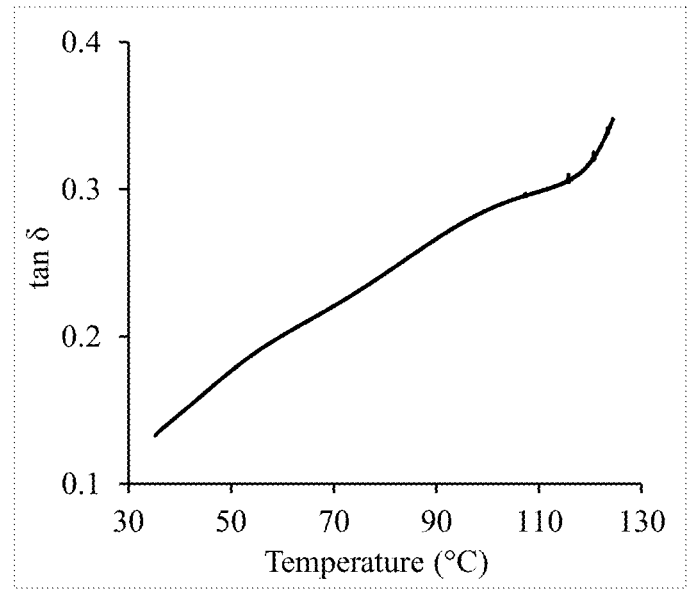
FIG. 1(b)

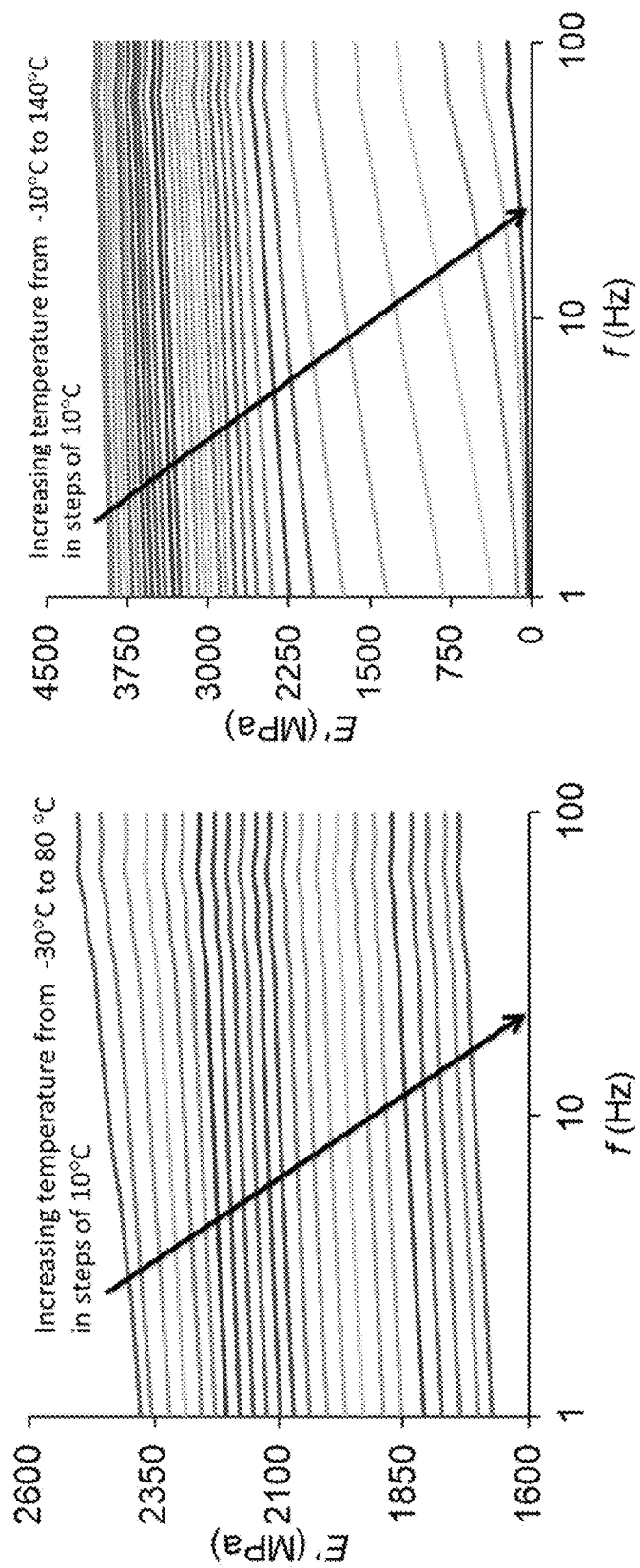

METHOD TO ESTIMATE STRAIN RATE DEPENDENT ELASTIC MODULUS OF MATERIALS USING DYNAMIC MECHANICAL ANALYSIS DATA

CROSS-REFERENCE TO RELATED APPLICATIONS

This application claims the benefit of and priority to U.S. Provisional Patent Application No. 62/375,315 filed on Aug. 15, 2016, the entire disclosure of which is incorporated by reference herein.

STATEMENT OF GOVERNMENT INTEREST

The United States Government claims certain rights in this invention pursuant to Office of Naval Research Contract No. N00014-10-1-0988.

TECHNICAL FIELD

The present disclosure relates generally to methods for measurement of mechanical properties, more specifically strain rate sensitivity estimation.

BACKGROUND

Despite the wide availability of dynamic mechanical analysis (DMA) results on polymers and composites, such data have rarely been applied to design of structures and components because the frequency-domain results obtained through this method are not directly applicable to most engineering problems. For thermosets, DMA is principally used to find maximum use and glass transition temperatures (Tg), which can determine the suitability of the material for application in a particular environment. However, for thermoplastics which are used above Tg, such as high density polyethylene (HDPE), and whose mechanical response is highly time-dependent (e.g., having an elastic modulus showing a change within quasi-static deformation rates of 0.0001-0.1/s), only having transition temperature information is not enough.

Measurement of properties at widely varying strain rates is often complicated by the limited speed ranges attainable within one testing setup or by a particular method. In addition, very low strain rate tests are time consuming and expensive to conduct, making it difficult to test multiple material samples at multiple strain rates and temperatures to develop a comprehensive understanding of mechanical properties of the material. Augmenting these present limitations, it is also noted that the correlation between results obtained from tensile or compressive tests with DMA results have not been established to develop a comprehensive understanding of the time and temperature dependent behavior of materials.

DMA provides storage modulus E' and loss modulus E" data. However, these two parameters are not usually parameters in engineering design. Instead, most engineering designs utilize Young's modulus (also known as the elastic modulus). Young's modulus is a measure of elasticity equal to the ratio of the stress acting on a material to the strain produced. In order to determine the Young's modulus, tensile and compression tests are conducted at very slow deformation rates ($10^{-6}$ to $10$ $s^{-1}$) using universal test machines. Tensile and compression tests are conducted at high strain rates (500 to 5000 $s^{-1}$) using split-Hopkinson pressure bar. Although Young's modulus can be calculated by this method at a high strain rate, the measurements are often not very reliable and the method is complicated. In addition, tensile and compression tests are done at various temperatures to obtain a full data set that describes material behavior over a wide range of strain rates and temperatures. High and low temperature split-Hopkinson pressure bar experiments are very complicated because temperature dependent correction factors are required for the wave speed and modulus of the bar material used in equipment, among other additional parameters needed to conduct calculations. Much of this information is not readily available in literature and needs additional experimentation. Measurement of properties at widely varying strain rates is often complicated by the limited speed ranges attainable within one testing setup or by a particular method. In addition, very low strain rate tests are time consuming and expensive to conduct, making it difficult to test multiple material samples at multiple strain rates and temperatures to develop a comprehensive understanding of mechanical properties of the material. Augmenting these present limitations, it is also noted that the correlation between results obtained from tensile or compressive tests with DMA results have not been established to develop a comprehensive understanding of the time and temperature dependent behavior of materials.

DMA is considered the most sensitive method to locate thermal transitions including those in crystallization and resin curing. When combined with other spectroscopy methods, information from DMA can reveal activation of different modes of motion of the polymer chains. DMA is also used to gain information on temperature sensitivity of the behavior of polymer blends, pharmaceutical and biomedical materials, and micro- and nano-composites. DMA data provides storage modulus E', loss modulus E", damping parameter tan δ, and glass transition temperatures $T_g$. However, the relation of the storage modulus E' and the loss modulus E" to Young's modulus (elastic modulus) at different strain rates has not been developed, which has been a major limitation in using DMA results in mechanical design.

A need exists for improved technology for transforming frequency-domain DMA data into a time-domain representation which can yield more readily useful information about the material behavior.

SUMMARY

In some implementations, a method for predicting an elastic modulus of a material, the method includes providing a sample in a dynamic mechanical analysis device, performing a temperature sweep test to obtain a first data set, performing a frequency sweep test to obtain a second data set, using the second data set to generate a master curve in a frequency domain of the at least one of the storage modulus of the sample or the loss modulus of the sample using time-temperature superposition, converting the master curve in the frequency domain into a time domain relaxation function, and using the time domain relaxation function to predict the elastic modulus of the material.

In some aspects, the temperature sweep test includes the steps of increasing a temperature of the sample from a predetermined minimum temperature to a predetermined maximum temperature while applying a cyclic force to the sample at a constant frequency; altering at least one of the storage modulus of the sample or the loss modulus of the sample while increasing the temperature; and measuring at least one of the storage modulus of the sample or the loss modulus of the sample to obtain the first data set. The cyclic force may be sinusoidal.

In some aspects, the frequency sweep test includes the steps of increasing the temperature of the sample from a second predetermined minimum temperature to a second predetermined maximum temperature in predetermined temperature increments; at each of the predetermined temperature increments, applying a cyclic force to the sample having a frequency that varies from a predetermined minimum frequency to a predetermined maximum frequency; altering at least one of the storage modulus of the sample or the loss modulus of the sample while increasing the frequency of the cyclic force applied to the sample; and measuring at least one of the storage modulus of the sample or the loss modulus of the sample at discrete frequencies spaced between the predetermined minimum frequency and the predetermined maximum frequency at each of the predetermined temperature increments to obtain the second data set. The cyclic force may be sinusoidal.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 1(a) illustrates storage and loss moduli results for HDPE resin from a DMA temperature sweep at 1 Hz.

FIG. 1(b) illustrates tan δ results for HDPE resin from a DMA temperature sweep at 1 Hz.

FIG. 15(a) illustrates a representative set of frequency sweeps for polycarbonate.

FIG. 15(b) illustrates a representative set of frequency sweeps for vinyl ester.

Figure 2:
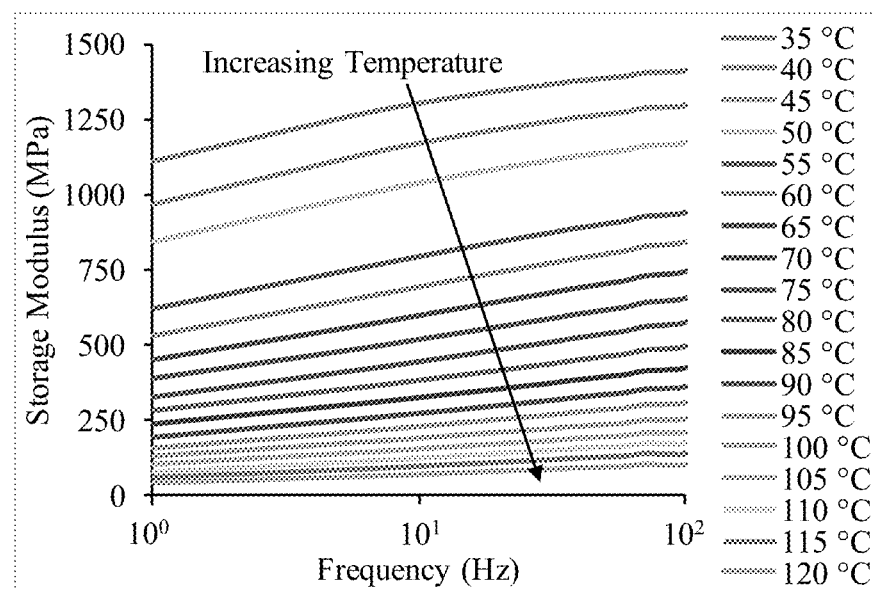
FIG. 2 illustrates a representative data set from combined temperature-frequency sweep on a material sample of HDPE.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made part of this disclosure.

DETAILED DESCRIPTION OF VARIOUS EMBODIMENTS

Dynamic mechanical analysis (DMA) is a technique in which a cyclic force (e.g., a sinusoidal force) is applied to a sample of known geometry to observe the sample's response. Typically, a force motor is used to generate a cyclic wave that is transmitted to the sample via a drive shaft. The sample's response to stress, temperature and frequency may be observed. DMA measures stiffness (modulus) and damping (tan δ). Because a cyclic force is applied, the modulus can be expressed as a storage modulus E' (an in-phase component) and a loss modulus E" (an out-of-phase component). The storage modulus E' is a measure of the sample's elastic behavior. The loss modulus E" is a measure of the sample's viscous behavior. The storage and loss moduli obtained from DMA provide a measure of energy stored and lost, respectively, in a material when a cyclic load-unloading profile is applied. Currently, there is no direct correspondence among E', E" and Young's modulus, which implies that knowing the values of E' and E" does not help in calculating the Young's modulus. Damping (tan δ) is the dissipation of energy in a material when a cyclic load-unloading profile is applied.

In general, embodiments of the present application are directed to a method that can use the dynamic mechanical analysis (DMA) data and convert the frequency-domain DMA data into time-domain data over a wide range of strain rates. In particular, the method may transform the frequency-domain DMA data to determine the Young's modulus (elastic modulus) over a wide range of strain rates. The method includes developing a correlation between frequency domain DMA results and elastic modulus values that are typically obtained from a separate set of elaborate tensile tests conducted over a wide range of strain rates. Using the time-temperature superposition principle and the integral relations of viscoelasticity, the DMA results are converted into a time-domain relaxation function in order to predict the strain-rate dependent elastic modulus. Cross-correlation between DMA results and tensile test results over a wide range of strain rates can help in substantially reducing the requirement for tests that are needed to characterize the material behavior with respect to strain rates, temperature and loading frequency.

Various material properties may be found from this transformed data, such as secant (or tangent) modulus at a given strain, and energy absorption at a given elastic strain. Various exact and approximate relations exist for converting this function to creep compliance as well. Using the time-temperature superposition (TTS) principle, a series of frequency sweeps at different temperatures are combined to yield the isothermal frequency response over a frequency range that is wide enough to ensure convergence of the transform over the desired strain rates.

The method for converting the DMA data into the elastic modulus over a wide range of strain rates is described in the examples below. One of ordinary skill in the art would appreciate that the method may be used to analyze a suitable material, for example, a polymer or polymer composite (e.g., polyethylene (HDPE), epoxy, vinyl ester or polycarbonate resin, or particle reinforced composites such as hollow particle filled syntactic foams). The material can be isotropic (e.g., syntactic foams) or anisotropic (e.g., fiber-reinforced composites). The method is not limited to the materials described in the examples below. In the case of isotropic materials, the properties measured in bending in the DMA are assumed to be the same as those measured in tension in strain rate sensitivity experiments. In the case of anisotropic materials, the material functions in different directions are determined from separate measurements and combined.

In Step S1, dynamic mechanical analysis (DMA) is conducted using a commercially available DMA analyzer (e.g., TA Instruments (New Castle, Del.) Q800 DMA). A material sample is placed inside of the DMA analyzer and a cyclic force is applied. The cyclic force may be sinusoidal. The DMA testing may be conducted in two phases: (1) using the temperature sweep mode at constant frequency, and (2) using the frequency sweep mode at constant temperature.

The results of phase (1) comprise a first data set, while the results of phase (2) comprise a second data set.

In phase (1) (i.e., the temperature sweep test), the temperature is ramped from a predetermined minimum temperature to a predetermined maximum temperature at a predetermined rate of temperature increase, with the deformation occurring at a constant frequency. The temperature sweep test helps in determining the temperature range for the frequency sweep test so that no peaks are missed. The temperature range is kept wide at this stage. For example, the temperature may be ramped from 35° C. to 130° C. at a rate of 1° C./min, while applying a sinusoidal force to the sample having a frequency of 1 Hz. Phase (1) may be halted once the storage modulus E' falls to a predetermined value (e.g., 20 MPa) to prevent total melting of the material sample inside of the DMA analyzer.

In phase (2) (i.e., the frequency sweep test), the temperature is stepped from a predetermined minimum temperature determined by either Tg or the application of the material to a predetermined maximum temperature determined by the melting temperature in predetermined increments determined by the thermal conductivity of the material. For example, the temperature may be stepped from 35° C. to 120° C. in increments of 5° C. At each temperature step, the material sample is held for a predetermined time (e.g., 5 minutes) to ensure thermal equilibrium. At each of the predetermined temperature increments or steps, a cyclic force is applied to the sample having a frequency that varies from a predetermined minimum frequency to a predetermined maximum frequency. The dynamic properties are measured at a predetermined number of discrete frequencies spaced between the predetermined minimum frequency and the predetermined maximum frequency at each temperature step. For example, the dynamic properties may be measured at 20 discrete frequencies logarithmically spaced between 1 and 100 Hz at each temperature step.

The first data (i.e., the temperature sweep results) help catch the transition temperatures and help determine the test temperature ranges according to the transitions. However, as described below, the results of the temperature sweep test are not required to generate the master curves. Therefore, in some aspects, the step of performing the temperature sweep results may be omitted from the method.

In Step S2, the results of the frequency sweeping and time-temperature superposition (TTS) principle are used to generate master curves describing the behavior of the material sample over a wider range of frequencies. According to the TTS principle, the effects of temperature and frequency variations are interchangeable. This principle allows for the extension of data collected over a limited frequency domain to be expanded by many orders of magnitude by applying a shift factor on the data collected over a range of temperatures. These curves are shifted to produce a master curve for the material based on a chosen reference temperature. Temperatures above the reference temperature shift to lower frequencies, while temperatures below the reference temperature shift to higher frequencies. These TTS shift factors are determined from the experimental data by shifting the curves obtained at different temperatures along the frequency axis to obtain a single smooth master curve. The shift factors for most polymers have been found to obey the Williams-Landel-Ferry (WLF) equation below:

$$\log_{10} a_T = \frac{-C_1(T - T_0)}{C_2 + T - T_0} \quad (1)$$

where $\alpha_T$ is the frequency shift factor, $C_1$ and $C_2$ are the WLF coefficients, T is the temperature each data set is acquired at, and $T_0$ is the reference temperature. Once the shift factors for a given material are determined, the corresponding WLF coefficients are independent of the choice of reference temperature. The values of $C_1$ and $C_2$ are found by fitting the WLF equation to the experimentally determined shift factors. The TTS parameters calculated for the storage modulus E' are also used for the loss modulus E" to construct master curves. The use of the same parameters to construct master curves provides validation for the values of these parameters and is one indication of thermorheological simplicity. Using the TTS principle, the storage modulus E' and the loss modulus E" are found over a sufficiently wide range of frequencies that can be used to adequately characterize a viscoelastic function of the material.

The resulting master curve represents the storage modulus E' at the reference temperature, but extended over a wider range of frequencies than accessible by the machine directly. However, this data still represents the steady state harmonic response, requiring the use of the transform procedure below (Step S3) to convert to an effective Young's modulus (elastic modulus) at different strain rates.

In Step S3, the viscoelastic function characterized by the frequency master curve produced in Step S2 is converted to a time domain relaxation function E(t). In particular, the frequency-domain viscoelastic function based on the storage modulus E' may, using an appropriate transformation, be converted to any other viscoelastic function which may be more useful for engineering and design purposes. From the storage modulus E', the time domain relaxation function E(t) can be found using the equation below:

$$E(t) = \frac{2}{\pi} \int_0^\infty \frac{E'(\omega)}{\omega} \sin(\omega t) d\omega \quad (2)$$

where $\omega$ and t represent angular frequency and time, respectively. To extrapolate the experimental data in the frequency domain, the storage modulus E' master curve at a chosen temperature is fitted to a sigmoidal function of log ($\omega$) of the form:

$$E'(\omega) = a \tan h(b(\log(\omega)+c))+d \quad (3a)$$

where a, b, c, and d are the fit coefficients and log($\omega$) is the natural logarithm. A fit of this form imposes that there is one smooth step transition in the storage modulus curve, corresponding to one peak in the loss modulus E", and that the behavior is asymptotic as frequency goes to zero to or positive infinity. Such choice satisfies the physically required positive and bounded behavior of the relaxation function at zero and infinite frequencies if d>a.

For the case where the experimental data captures multiple transitions, a mixture of functions of this form can be applied. For example, to extrapolate the experimental data in the frequency domain, the storage modulus master curve at a chosen temperature is fitted to a mixture of sigmoidal functions of log($\omega$) of the form:

$$E'(\omega) = c_1 + \Sigma_{j=1}^N c_{j1} \tan h(c_{j2} \log(\omega)+c_{j3}) \quad (3b)$$

where the c's are the fit coefficients and log($\omega$) is the natural logarithm. A fit of this form imposes that there are N smooth step transitions in the storage modulus curve, each corresponding to a peak in E", and that the behavior is asymptotic as frequency goes to zero or to positive infinity. N can be chosen by examining the number of peaks in the E" master curve, as the step transitions often overlap on the E' master curve. This form provides a more compact representation than the Prony series model because each relaxation process requires only three extra coefficients, while a large number of exponential functions are required to model each relaxation. However, this function is not guaranteed to satisfy the nonnegative requirement that results from thermodynamics unless $c_1 \geq \Sigma c_{j1}$.

The frequency at which $E'(\omega)=0$ and below which E' is negative is:

$$\omega |_{E'=0} = \exp\left[\frac{-bc - a\tanh(d/a)}{b}\right] \quad (4)$$

Equation (4) is of the order $10^{-16}$ Hz for the both syntactic foams described in Experiment 2 below. While it is simple to enforce that $E'(\omega)=0$ in the curve fitting, this yields a poorer fit in the moderate frequency ranges which are most important to the response. In the unconstrained fit, the frequency at which the function is negative is sufficiently small that the negative E' will not substantially affect the resulting relaxation function, so the parameters from the unconstrained fit are used in the subsequent analysis.

The transform in Equation (2) of the fitting function is integrated numerically to yield the time domain relaxation function for the material. The time domain relaxation function can be observed to satisfy the requirements of fading memory and nonnegative stored and dissipated energy as expressed in the equation below:

$$E(t) \geq 0, \frac{dE(t)}{dt} \leq 0, d^2 E(t)/dt^2 \geq 0 \quad (5)$$

within the range of times displayed. Since d<a in the fitted functions, at some time the relaxation function will violate the first condition and yield a negative value for E(t). However, this crossover is observed well beyond practical time scales.

The time-domain relaxation function determines the stress history generated by a specified strain history when convolved with a strain history function according to the equation below:

$$\sigma(t) = E \times d\varepsilon = \int_{-\infty}^t E(t-\tau)\frac{d\varepsilon(\tau)}{d\tau}d\tau \quad (6)$$

where $\sigma$, $\varepsilon$ and $\tau$ represent stress, strain and time variable used for integration, respectively. For constant strain rate deformation with a strain rate of $\dot{\varepsilon}$ beginning at t=0, which is the idealized deformation state in a standard tension test, the convolution integral simplifies to:

$$\sigma(t) = \dot{\varepsilon} \int_{-\infty}^t E(\tau) d\tau \quad (7)$$

Using this method, the linear viscoelastic stress-strain response of the materials can be predicted for any strain rate. In particular, the elastic modulus calculated from this equation can be expressed as elastic modulus at various strain rates and corresponds to the values measured from tensile tests conducted at those strain rates.

In an optional Step S4, the range of strain rates for which the predicted modulus obtained from tensile tests can be matched with the predictions obtained from transforming the DMA data from frequency-domain to time-domain is determined. In other words, the limits on the strain rates for which such predictions would be valid from a given set of DMA data is derived. Within this region, the prediction is determined primarily by the master curve, rather than by the extrapolated curve. The accuracy of the time-domain relaxation function outside of the experimentally measured frequencies depends on the appropriateness of the fit function in the extrapolated regions. Therefore, the presence of additional transitions, which are not measured experimentally, will cause some deviation from the true relaxation function. When using the lowest temperature as the reference for the master curve, the maximum frequency of the TTS spectrum equals the maximum frequency attained in the experiment. An approximation of the smallest time scale for which the relaxation function corresponds to the experimental data can be attained according to the following equation:

$$t \to 2\pi/\omega \qquad (8)$$

At times earlier than the time calculated using Equation (8), the relaxation function is primarily influenced by the extrapolated values of the storage modulus curve, which would correspond to lower temperature data. Since it is known that there are further transitions in the storage modulus curve below the lowest temperature measured in the experiments described below, without accounting for these transitions, the relaxation function obtained is an underestimate on shorter time scales. With one transition captured, the modulus-strain rate function appears as a sigmoid. If there is more than one transition, a function other than a sigmoidal function may be needed. The missing transitions also lead to missing curvatures in the modulus-strain rate function. Thus for accurate high strain rate predictions, DMA frequency sweeps must be performed at temperatures below the reference temperature. Experimental measurement of higher strain rate properties is conducted by the split-Hopkinson pressure bar technique, which has been used to measure mechanical properties of materials at strain rates up to about $5 \times 10^3$ s$^{-1}$. Deformation time scales obtained in those experiments are much smaller than the limit obtained by Equation (8). For such case with multiple transitions, a similar fit function may be applied multiple times over successive frequency domains and integrated separately to yield the overall relaxation function, so long as each of the separate transforms is convergent. These predictions can be useful in mechanical and structural design as strain rate is an integral part of those calculations.

According to the method described above, it is possible to convert the storage modulus and loss modulus results obtained from dynamic mechanical analysis to elastic modulus values at different strain rates. Using the TTS principle, the limited set of results obtained from DMA is expanded around a single temperature to cover a much wider range of frequencies. This frequency spectrum is then inverted to the time-domain relaxation function, which can yield accurate predictions of the linear viscoelastic response of the materials. Cross-correlation between DMA results and tensile test results over a wide range of strain rates can help in substantially reducing the requirement for tests that are needed to characterize the material behavior with respect to strain rates, temperature and loading frequency.

In some aspects, the Kramers-Kronig (K-K) relations can be used to obtain the loss modulus function E"(ω) that corresponds to a given function for E'(ω) via the following integral transform $$E''(\omega) = \frac{2\omega}{\pi} \int_0^\infty \frac{E'(\lambda) - E'(\omega)}{\lambda^2 - \omega^2} d\lambda \qquad (9)$$

which can be approximated by $$E''(\omega) \approx \frac{\pi}{2} \frac{dE'(\omega)}{d\ln\omega}. \qquad (10)$$

The K-K relations are used to compute a prediction of the loss modulus that corresponds to the fitted storage modulus function. This prediction is compared to the experimental loss modulus master curve to assess how well the fitted function represents the actual material behavior. This method for comparing is advantageous because weak transitions are difficult to discern from the storage modulus curve, where they appear as small kinks in the curve. However, transitions appear as peaks on the loss modulus curve, and so are easier to discern. The presence of transitions outside of the experimental data range also causes substantial deviations from the K-K prediction, which makes it easy to determine if the experimental data has covered a wide enough range of frequency.

Though the transform could be integrated numerically, and more accurate but complex approximations exist, this simple form has been found to be widely applicable and allows the use of an analytical form using the fitting function selected here. Based on the approximation of the K-K relations, the sigmoidal storage modulus function yields the loss modulus function $$E''(\omega) = \frac{\pi ab}{2} \text{sech}(b(\log(\omega) + c)^2 \qquad (11)$$

which will be referred to as the "K-K prediction." The frequency at which this is maximal, $\omega_T$, and which is the typical definition of the location of the transition, is found to be $$\omega_T = \exp\left(\frac{1}{c}\right) \qquad (12)$$

Thus, one can obtain a frequency-temperature pair that corresponds to a transition. The transition temperature corresponding to this transition at another frequency can be found using the WLF equation (Equation (1)) and its experimentally determined coefficients. Since transition temperatures are usually defined at 1 Hz, this method could be used to find transitions that are below the temperature range of the test equipment by using the higher frequency data and TTS to extend the range. The magnitude of the extension of the temperature range by this technique would depend on the TTS shift factors, which quantify the relationship between changes in frequency and changes in temperature. The shift factors outside the experimental temperature range can be estimated by the WLF or Arrheius equations, as applicable. The fit parameter b is related to the breadth or "sharpness" of the transition.

Experiment 1

In one example, the method is validated by comparing predictions with reported values for high density polyethylene (HDPE) resin in the literature. HDPE was chosen due to its widespread use in manufacturing industrial products and extensive use as a matrix resin in polymer matrix composites. The HDPE used in the experiment had a melt flow index of 20 g/10 min (190° C./2.16 kg). The resin was in granular form of 3 mm diameter and had a mean molecular weight of 97,500 g mol$^{-1}$. The samples had dimensions of 60 mm×12.7 mm×3.3 mm (length×width×height).

In Step S1, dynamic mechanical analysis (DMA) was conducted using a TA Instruments (New Castle, Del.) Q800 DMA analyzer. The HDPE samples were tested in a dual cantilever configuration with a span length of 35 mm. Testing was conducted in the strain control mode with a maximum displacement of 25 μm. In phase (1) (i.e., the temperature sweep test), the temperature was ramped from 35° C. to 130° C. at a rate of 1° C./min, with the deformation occurring at 1 Hz. Phase (1) was halted once the storage modulus E' reached a value of 20 MPa to prevent total melting of the HDPE sample inside of the DMA analyzer. In phase (2) (i.e., the frequency sweep test), the temperature was stepped from 35° C. to 120° C. in increments of 5° C. At each temperature step, the material sample was held for 5 minutes to ensure thermal equilibrium. The dynamic properties were measured at 20 discrete frequencies logarithmically spaced between 1 and 100 Hz at each temperature step. At least three samples of HDPE were tested.

Results—Phase 1 Temperature Sweep

A representative set of results of the temperature sweep for E', E", and tan δ for one HDPE sample is shown in FIGS. 1(a) and 1(b). Results on E', E", and tan δ were extracted at three representative temperatures in the rubbery plateau region of 60, 80 and 100° C. and are presented in Table 1 below.

TABLE 1

| Property | 60° C. | 80° C. | 100° C. |
| --- | --- | --- | --- |
| E' (MPa) | 572.88 ± 4.1 | 292.59 ± 3.7 | 135.53 ± 3.4 |
| E" (MPa) | 115.05 ± 0.9 | 70.63 ± 0.7 | 38.43 ± 0.9 |
| tan δ (×10$^{-2}$) | 20.08 ± 0.07 | 24.14 ± 0.19 | 28.35 ± 0.32 |

The trends of E" with respect to temperature are presented in FIG. 1(a) for HDPE resin. The peak in E" at around 50° C. corresponds to the α-relaxation in HDPE, which is associated with softening of the interface between crystallites and the amorphous phase. Tan δ results are presented in FIG. 1(b). Tan δ, also known as the damping parameter, loss factor or loss tangent, is the ratio of the E" to the E' and represents the relative magnitudes of the elastic and viscous behavior of the material. Although no transition peaks were observed in the test temperature range used in this experiment, previous studies have shown that α-, β-, and γ-transition peaks appear in the low temperature regions. These peaks correspond to relaxation of polymer chain and loss of crystallinity to form an amorphous phase. Increase in temperature from room temperature to higher temperatures results in a decrease in E' and E" because of the increase in the polymer chain mobility. The damping parameter increases with increasing temperature over the range shown here, as the elastic component of the response disappears as melting is approached, while the viscous component remains.

Results—Phase 2 Frequency Sweep

In phase (2) of the DMA analysis, isothermal frequency sweeps were conducted in the range of temperatures from 35 to 120° C. A representative set of DMA curves obtained by varying frequency at various temperature steps for HDPE resin is shown in FIG. 2. The trends show that E' increases with frequency, which indicates strain rate sensitivity in the material due to its viscoelastic nature. It was also observed that the frequency dependence of E' diminishes as temperature increases due to the increased resin flow characteristics.

In Step S2, the results of the frequency sweeping and time-temperature superposition (TTS) principle are used to generate master curves describing the behavior of the HDPE sample over a wider range of frequencies. Referring to Equation (1), the values for $C_1$ and $C_2$ were found to be 33±4 and 322±34 K, respectively, by fitting the WLF equation to the experimentally determined shift factors. The TTS parameters calculated for E' were also used for E" to construct master curves. The shift factors for HDPE were similar to those reported in the literature. However, direct comparison of the shift factors for HDPE requires caution as they are affected by the degree of crystallinity and molecular weight.

Figure 3:
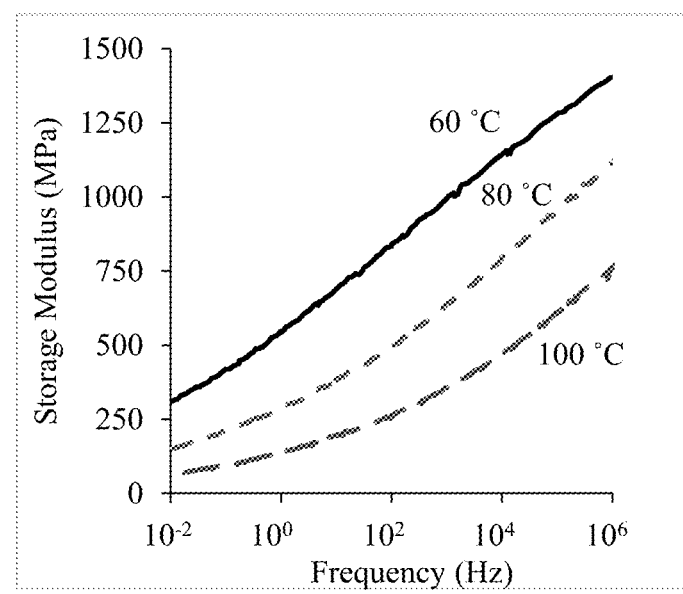
FIG. 3 illustrates time-temperature superposition results from a DMA frequency sweep calculated for arbitrarily selected reference temperatures of 60, 80, and 100° C.

The master curves for E' of HDPE resin at three representative temperatures are shown in FIG. 3. The curves are shown in the frequency range of $10^{-2}$ to $10^{-6}$ Hz, which is the range encountered in most vibration sensitive applications. However, the curves can be plotted for a much wider frequency range. Using the TTS principle, the storage modulus E' and the loss modulus E" were found over a sufficiently wide range of frequencies and used to adequately characterize a viscoelastic function of the HDPE.

Figure 4:
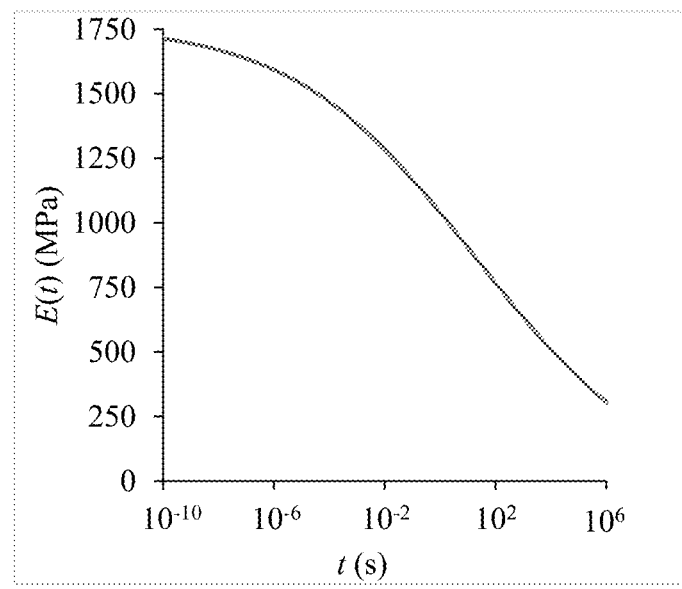
FIG. 4 illustrates a time domain relaxation function determined using the transform in Equation (2) for HDPE.

In Step S3, the viscoelastic function was converted to the time-domain. Using Equations (2)-(7), the linear viscoelastic stress-strain response of the HDPE can be predicted for any strain rate. The time domain relaxation function of HDPE determined using the transform in Equation (2) is illustrated in FIG. 4. The $R^2$ value of the curve fit to the master curve was above 0.999, indicating an appropriate fit.

According to the American Society for Testing and Materials (ASTM D790-17), the secant modulus is the ratio of stress to corresponding strain at any selected point on the stress-strain curve, that is, the slope of the straight line that joins the origin and a selected point on the actual stress-strain curve. The secant modulus is expressed in megapascals (pounds per square inch). The selected point is chosen at a pre-specified stress or strain in accordance with the appropriate material specification or by customer contract. Many polymers like HDPE do not have a straight line elastic region in their tensile stress-strain graph where Young's modulus can be calculated. Instead, the graph looks like a curve. In such materials, the secant modulus is calculated and assumed to be the same as Young's modulus.

Figure 5:
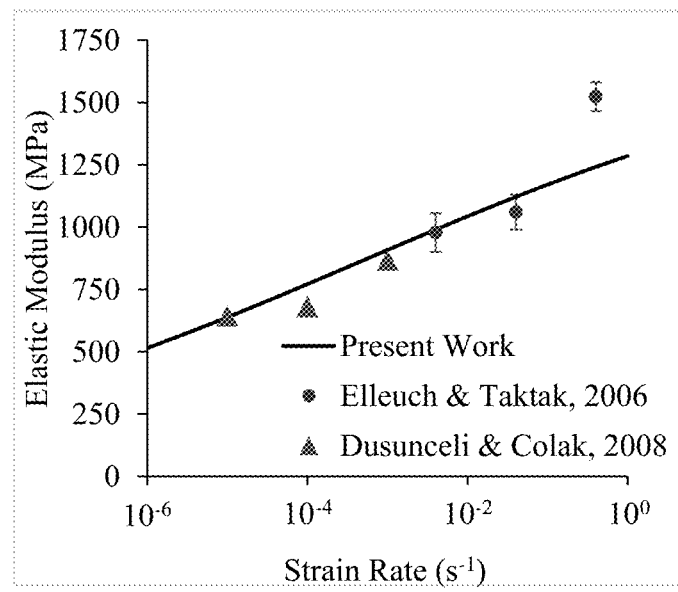
FIG. 5 illustrates a comparison of modulus predictions from the time domain relaxation function of FIG. 4 with literature values for HDPE.

To confirm the validity of the method, data for HDPE was compared with values found in the literature, as seen in FIG. 5. The predictions of elastic modulus were evaluated as the secant modulus at 2.5% strain from the stress-strain values generated from the relaxation function, which were approximately the same as the definitions used in the literature. At strain rates of $10^{-5}$ to $4\times10^{-2}$ s$^{-1}$, the prediction from transformation of the DMA results was in close agreement with the literature values, while at the strain rate of $4\times10^{-1}$ s$^{-1}$, the prediction deviated by about 20% from the experiments.

When using the lowest temperature as the reference for the master curve, the maximum frequency of the TTS spectrum equals the maximum frequency attained in the experiment. Thus, the upper limit for this experiment was 100 Hz and room temperature was the reference temperature. Using Equation (8), the smallest time scale for which the relaxation function corresponds to the experimental data was determined to be 0.063 s. At times earlier than this, the relaxation function is primarily influenced by extrapolated values of the storage modulus curve which would correspond to lower temperature data. At a strain rate of $4\times10^{-1}$ s$^{-1}$, a strain of 2.5% was reached in 0.0625 s, so that the data for 2.5% secant modulus at this and any higher strain rates was derived mainly from the extrapolation.

In summary, the experiment found that storage modulus decreases with increasing temperature in the range of 35-120° C., while tan δ increases. In addition, loss modulus reaches a peak around 50° C., which corresponds to the a-relaxation. Using the frequency spectrum from TTS, the time-domain relaxation function was obtained and used to predict the viscoelastic behavior as a function of strain rate, and was found to be in good agreement with experimental data on the strain rate sensitivity of HDPE from the literature over a wide range of strain rates ($10^{-5}$ to $4\times10^{-2}$ s$^{-1}$). An approximation of the highest strain rate (shortest time scale) for which the predictions are valid was determined. Conducting DMA runs at lower temperatures can improve the accuracy of predictions at higher strain rates.

Experiment 2

Figure 7B:
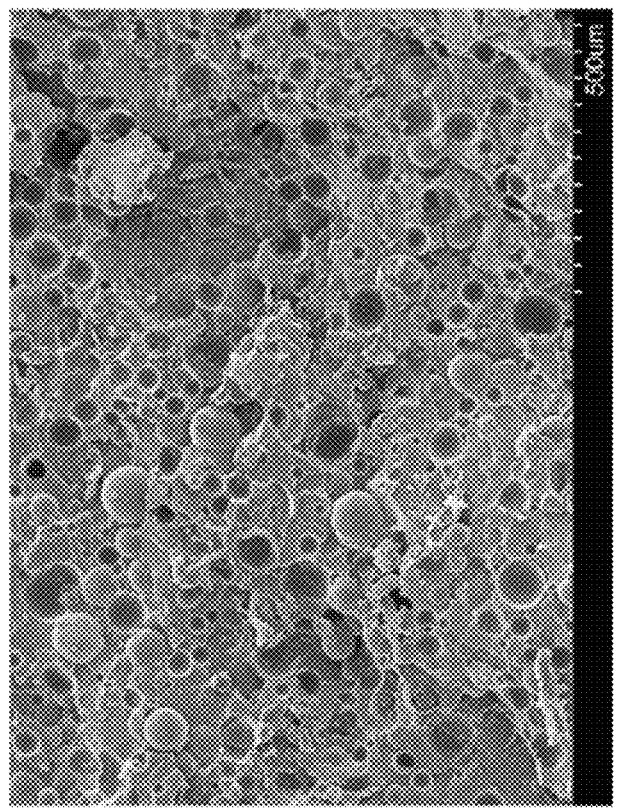
FIG. 7(b) is a scanning electron micrograph of a HDPE40 (containing 40 wt. % hollow particles in HDPE resin) freeze-fractured surface showing uniform distribution of hollow particles.
Figure 7A:
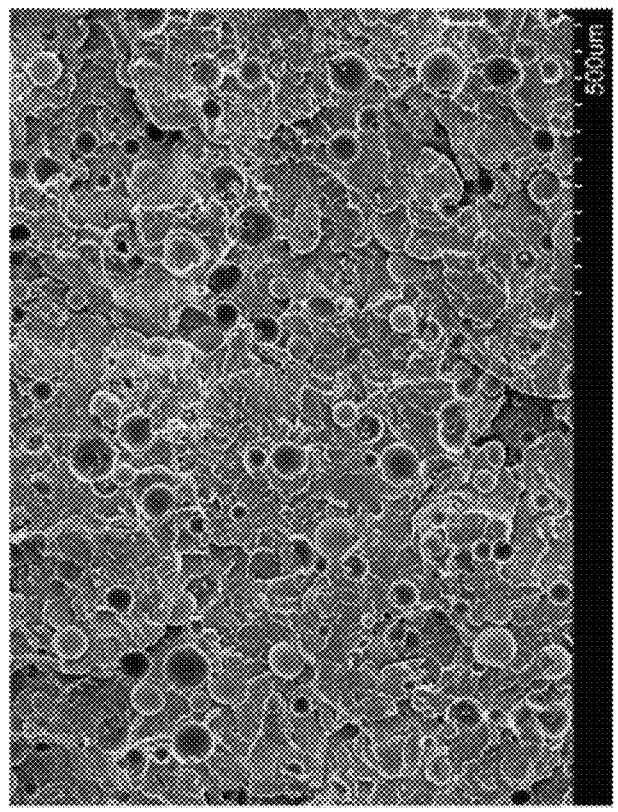
FIG. 7(a) is a scanning electron micrograph of a HDPE20 (containing 20 wt. % hollow particles in HDPE resin) freeze-fractured surface showing uniform distribution of hollow particles.

In another example, the method was performed using high density polyethylene (HDPE) matrix fly ash cenosphere reinforced composites called syntactic foams. In particular, HDPE of grade HD50MA180 was used as the matrix materials. The HDPE had a melt flow index of 20 g/10 min (190° C./2.16 kh) and a mean molecular weight of 97,500 g mol$^{-1}$. Cenospheres of CIL-150 grade were used as hollow fillers. One of ordinary skill in the art would have understood that other grades of HDPE and cenospheres may be used. The cenospheres were used in the as-received condition, without any surface treatment. The cenospheres comprise alumina, silica, calcium oxide and iron oxides. The cenospheres were used in 20 and 40 wt % in HDPE to fabricate two types of syntactic foams, HDPE20 and HDPE40, restively, on a polymer injection molding (PIM) machine. Operating and processing parameter of the PIM machine were set at 160° C. temperature and 30 kg/cm$^2$ (2.9 MPa) pressure. Samples of dimensions 60 mm×12.7 mm×3.3 mm (length×width×height) were molded. The length of the samples was later reduced by cutting with a diamond saw to 35 mm. Scanning electron micrographs of freeze-fractured surfaces of the syntactic foams are illustrated in FIG. 7(a) (HDPE20) and FIG. 7(b) (HDPE40). Fly ash cenospheres are observed to be distributed uniformly throughout the syntactic foam. Various factors such as matrix porosity entrapment, particle crushing and quality of particle-matrix interface depend on the sample fabrication method. These factors affect the mechanical properties, including elastic and viscoelastic properties of syntactic foams.

Dynamic mechanical analysis (DMA) was conducted using a TA Instruments (New Castle, Del.) Q800 DMA analyzer. The syntactic foam samples were tested in a single cantilever configuration with a span length of 17.5 mm. Testing was conducted in the strain control mode with a maximum displacement of 25 μm. In phase (1) (i.e., the temperature sweep test), the temperature was ramped from −100° C. to 130° C. at a rate of 1° C./min at a constant frequency of 1 Hz. In phase (2) (i.e., the frequency sweep test), the temperature was stepped from −10° C. to 130° C. in increments of 5° C. At each temperature step, the material sample was held for 8 minutes to ensure thermal equilibrium. The dynamic properties were measured at 20 discrete frequencies logarithmically spaced between 1 and 100 Hz at each temperature step. Testing was halted if E' dropped below 10 MPa, in order to prevent melting of the sample in the DMA analyzer. At least three samples of each syntactic foam were tested.

Figures 8A, 8B:
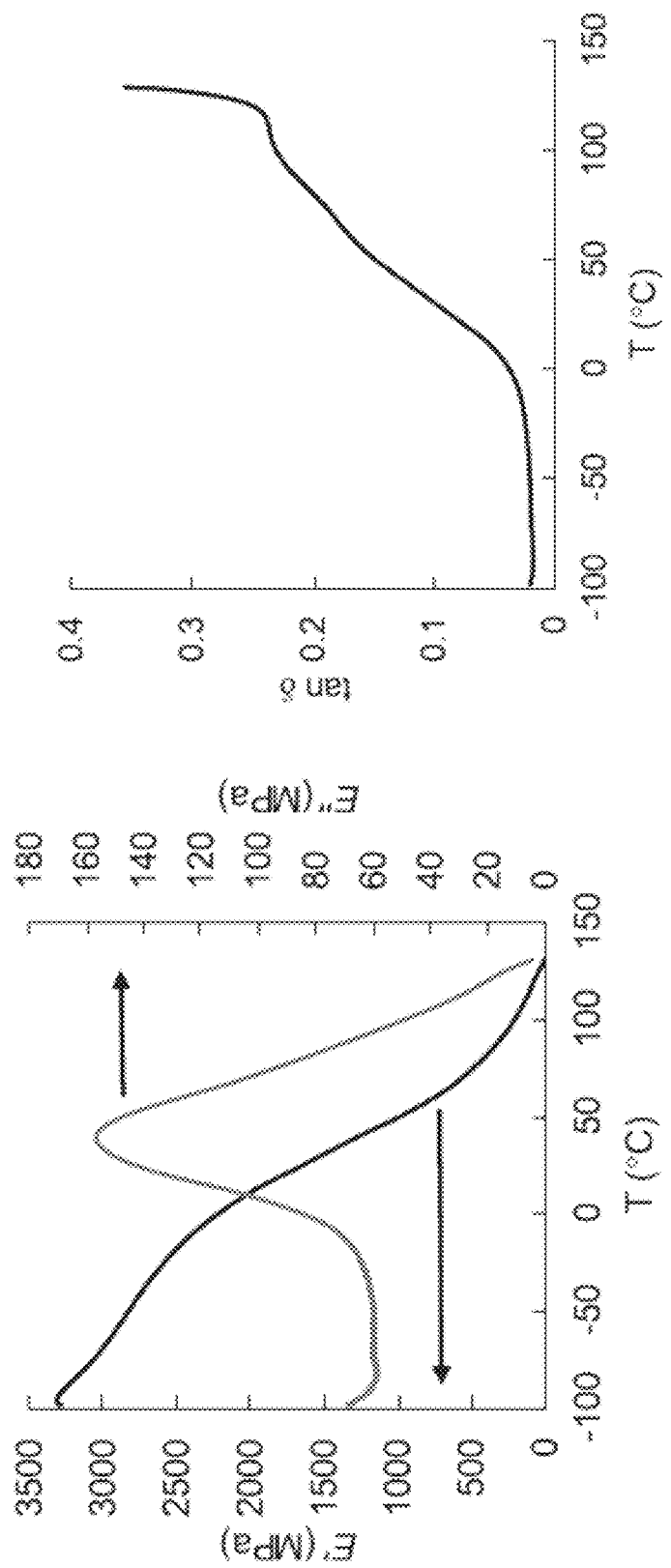
FIG. 8(a) illustrates storage and loss moduli results for HDPE20 syntactic foam from a DMA temperature sweep at 1 Hz.
FIG. 8(b) illustrates tan δ results for HDPE20 syntactic foam from a DMA temperature sweep at 1 Hz.
Figures 9A, 9B:
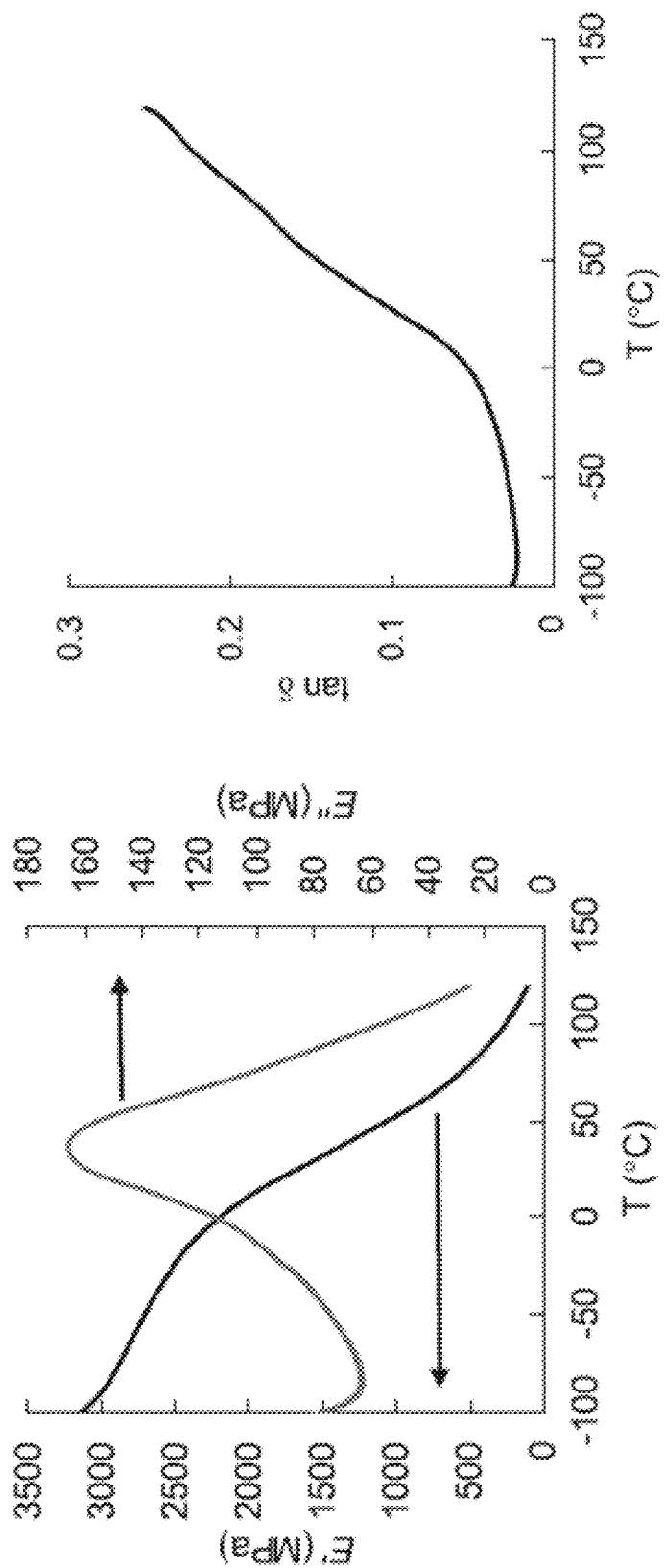
FIG. 9(a) illustrates storage and loss moduli results for HDPE40 syntactic foam from a DMA temperature sweep at 1 Hz.
FIG. 9(b) illustrates tan δ results for HDPE40 syntactic foam from a DMA temperature sweep at 1 Hz.
Figure 10:
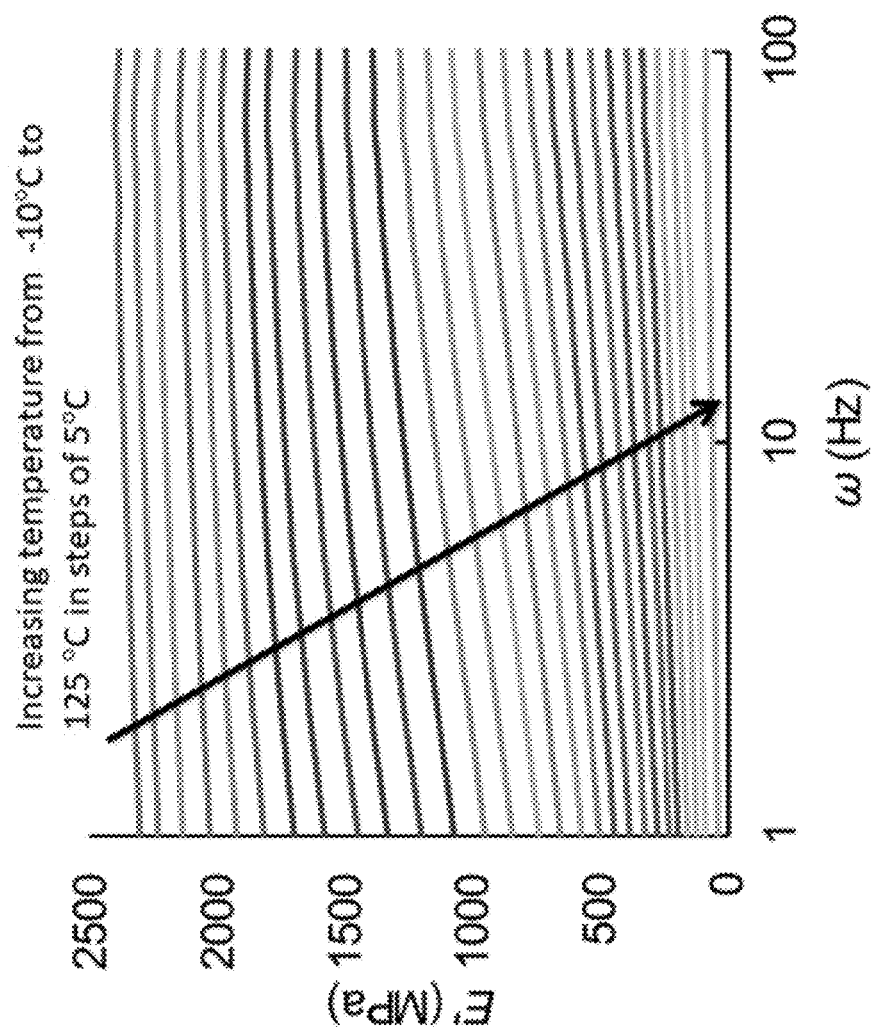
FIG. 10 illustrates a representative set of frequency sweeps for HDPE40 syntactic foam.

Results from the temperature sweep at 1 Hz are shown in FIGS. 8(a) and 8(b) for HDPE20 and in FIGS. 9(a) and 9(b) for HDPE40. Both syntactic foams have a peak in the loss modulus E" at about 37° C., which is due to the a-transition in HDPE. Based on the loss modulus peak or the increase in tan δ, the onset of this transition is at about 0° C. The transition continues until the HDPE is melted. At −100° C., there is evidence of another peak in the loss modulus E", though the data did not include low enough temperatures to fully capture this peak. The peak in HDPE at −110° C. is generally associated with the glass transition. Since the HDPE is above its $T_g$ and within the α-transition range at room temperature, strong strain rate sensitivity in its mechanical properties were expected. A set of representative frequency sweeps for HDPE20 is presented in FIG. 10.

Figure 11:
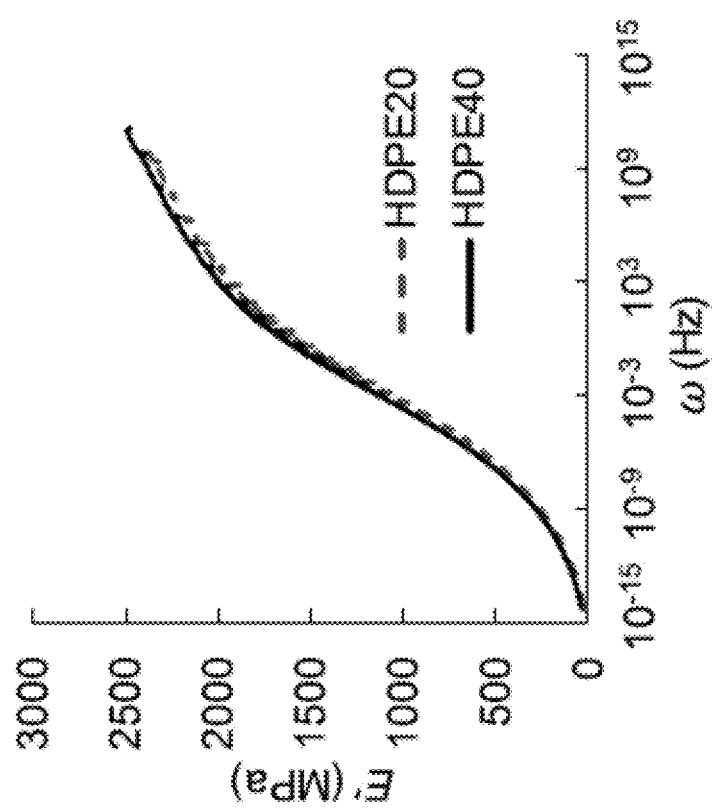
FIG. 11 illustrates storage modulus master curves constructed using 25° C. as the reference temperature for HDPE20 and HDPE40 syntactic foams.

The results of the frequency sweeping and time-temperature superposition (TTS) principle are used to generate master curves describing the behavior of the HDPE sample over a wider range of frequencies. FIG. 11 illustrates the storage modulus master curves constructed using 25° C. as the reference temperature for the HDPE20 and HDPE40 syntactic foams.

Figure 13:
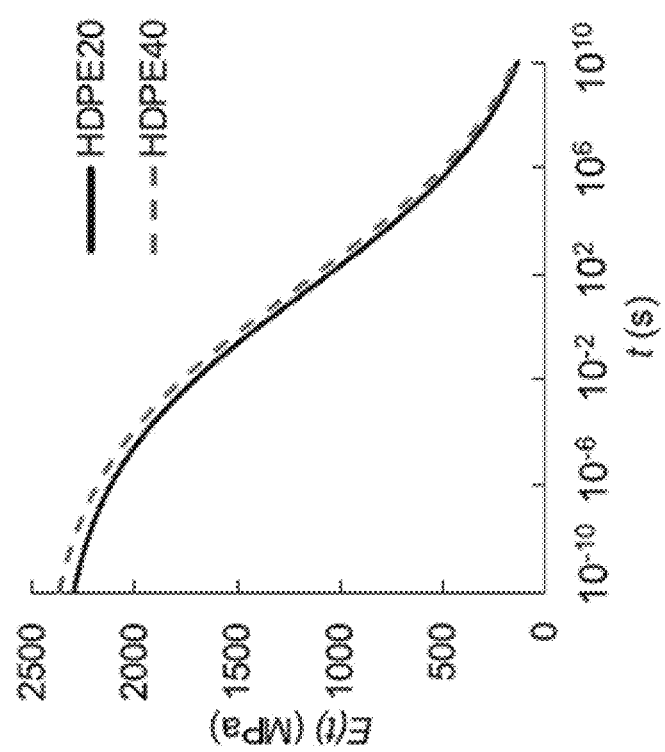
FIG. 13 illustrates time domain relaxation functions for HDPE syntactic foams at 25° C.

The viscoelastic function was converted to the time-domain. Using Equations (2)-(7), the linear viscoelastic stress-strain response of the syntactic foams can be predicted for any strain rate. The time domain relaxation function of the syntactic foams determined using the transform in Equation (2) is illustrated in FIG. 13.

Figure 12A:
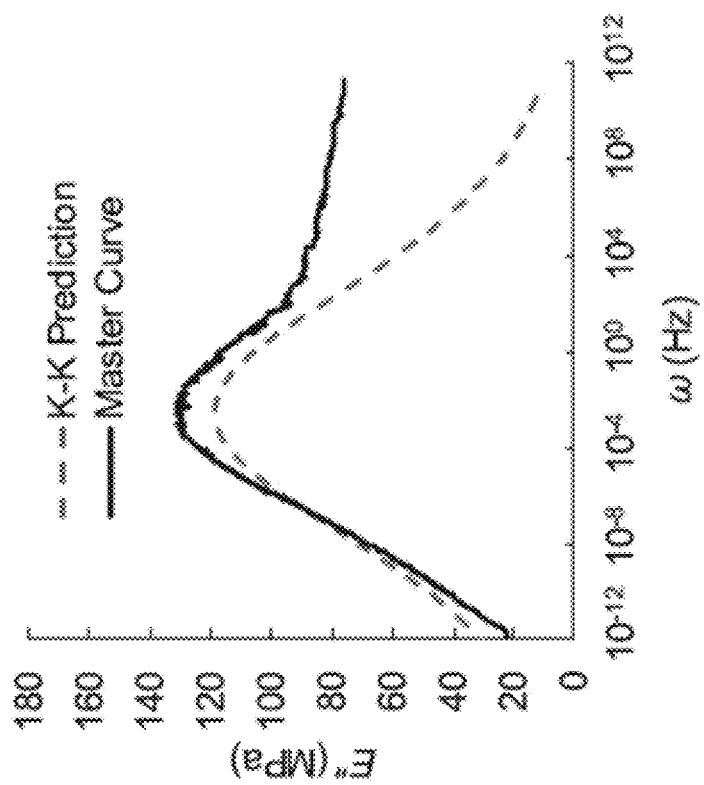
FIG. 12(a) illustrates a comparison of the experimental loss modulus master curve at 25° C. with the predictions of the approximate K-K relations, using the coefficient of the fit function for HDPE20.
Figure 12B:
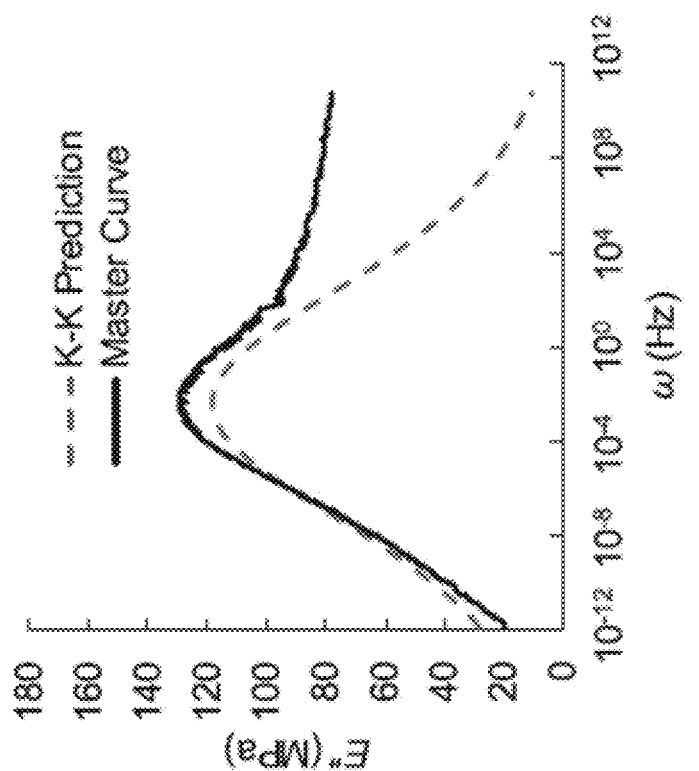
FIG. 12(b) illustrates a comparison of the experimental loss modulus master curve at 25° C. with the predictions of the approximate K-K relations, using the coefficient of the fit function for HDPE40.

FIGS. 12(a) and 12(b) illustrates the K-K prediction of the loss modulus curve (Equation 11) compared to the experimentally determined loss modulus master curves at 25° C. for HDPE20 and HDPE40, respectively. The loss modulus master curves are constructed by shifting the loss modulus curves from the frequency sweeps using the shift factors determined from shifting the storage modulus curves. At frequencies below the peak, excellent agreement is observed between the prediction and the master curve. However, above the peak, the K-K prediction trends towards zero, while the master curve remains higher. This is likely due to the presence of another peak at higher frequencies (lower temperatures) than what was captured in the frequency sweep experiments. The use of the K-K prediction in comparison to the experimental loss modulus master curve is a more sensitive means to assess the goodness of fit, since transitions near the minimum and maximum frequency are difficult to discern from the storage modulus master curve. Such deviations appear clearly on the loss modulus master curve, since the loss modulus shows peaks at these transitions.

Experiment 3

In another example, the method was performed using polycarbonate (PC) sheets having dimensions of 45 cm×30 cm×0.328 cm (length×width×height). Dynamic mechanical analysis (DMA) was conducted using a TA Instruments (New Castle, Del.) Q800 DMA analyzer. The PC sheet samples were tested in a single cantilever bending configuration with a span length of 17.5 mm. In phase (1) (i.e., the temperature sweep test), the temperature was ramped from −100° C. to 150° C. at a rate of 1° C./min at a constant frequency of 1 Hz. In phase (2) (i.e., the frequency sweep test), the temperature was stepped from −30° C. to 80° C. in increments of 5° C. At each temperature step, the material sample was held for 8 minutes to ensure thermal equilibrium. The dynamic properties were measured at 20 discrete frequencies logarithmically spaced between 1 and 100 Hz at each temperature step.

Figures 14A, 14B:
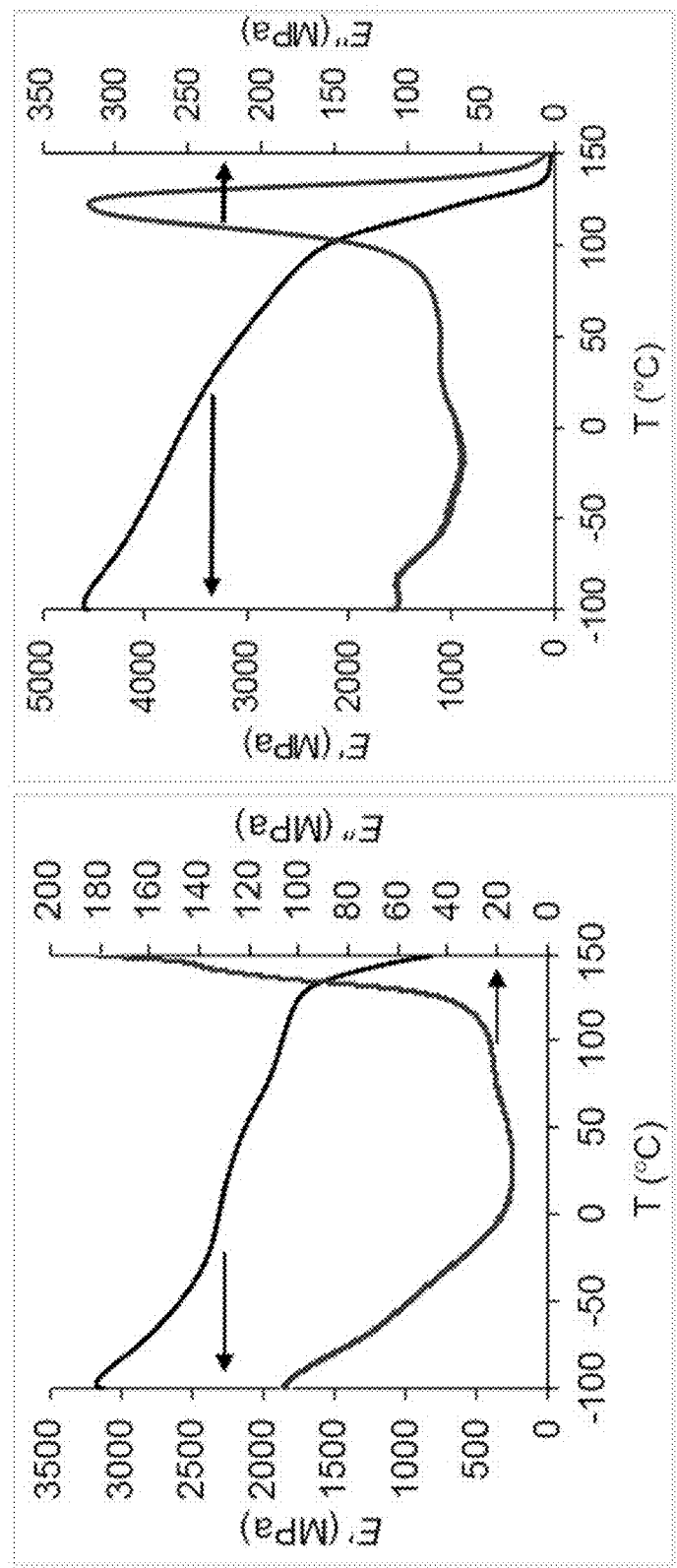
FIG. 14(a) illustrates storage and loss moduli results for polycarbonate from a DMA temperature sweep at 1 Hz.
FIG. 14(b) illustrates storage and loss moduli results for vinyl ester from a DMA temperature sweep at 1 Hz.

Representative temperature sweep results for the PC samples are shown in FIG. 14(A). The PC sheets undergo a glass transition at around 148° C. and a β-transition around −100° C. The storage modulus decreases monotonically with increasing temperature as PC does not exhibit entropic elasticity. Representative frequency sweep results for the PC samples are shown in FIG. 15(A). The storage modulus E' increases with increasing frequency and decreases with increasing temperature.

The TTS principle was applied, as described above, to form a master curve shown in FIG. 14(B). In the PC master curve, evidence of two peaks was observed, but neither peak was fully captured due to the limited temperature range feasible for performing temperature sweeps. The frequency master curve was then converted into a time domain relaxation function E(t) using the equations described above. The $R^2$ value of the curve fit to the master curve is above 0.99, indicating an appropriate fit. The zero-frequency asymptote is around 900 MPa. From the stress-strain curve that results, various properties of interest can be calculated. The Young's modulus (elastic modulus) was estimated by evaluating the second modulus at 0.5% strain, since the elastic region for viscoelastic materials is usually not linear. The predictions of the secant modulus were compared with tensile experiments, which agreed well with the prediction (i.e., the predictions were within ±10% of the values measured in the tensile experiments). The upper limit on the strain rate for which the Young's modulus obtained from tensile tests can be matched with the predictions obtained from transforming the DMA data from frequency-domain to time-domain data was $10^9$ s$^{-1}$.

As part of Experiment 3, the method was also performed using polyvinyl ester (VE). 700 vinyl ester (VE) resin was catalyzed at 1% (by volume) with methyl ethyl ketone peroxide (MEKP). The vinyl ester was fabricated by casting in aluminum molds and curing at room temperature for 24 hours and at 90° C. for 1 hour. Rectangular specimens of 35 mm×11.64 mm×2.84 mm were machined for the DMA samples. Dynamic mechanical analysis (DMA) was conducted using a TA Instruments (New Castle, Del.) Q800 DMA analyzer. The VE samples were tested in a single cantilever bending configuration with a span length of 17.5 mm. In phase (1) (i.e., the temperature sweep test), the temperature was ramped from −100° C. to 170° C. at a rate of 2° C./min at a constant frequency of 1 Hz. In phase (2) (i.e., the frequency sweep test), the temperature was stepped from −10° C. to 140° C. in increments of 5° C. At each temperature step, the material sample was held for 8 minutes to ensure thermal equilibrium. The dynamic properties were measured at 20 discrete frequencies logarithmically spaced between 1 and 100 Hz at each temperature step.

Representative temperature sweep results for the VE samples are shown in FIG. 14(B). The VE samples have a glass transition at around 120° C. and a β-transition around −75° C. The storage modulus decreases monotonically with increasing temperature as PC does not exhibit entropic elasticity. Representative frequency sweep results for the PC samples are shown in FIG. 15(B). The storage modulus E' increases with increasing frequency and decreases with increasing temperature.

Figures 16A, 16B:
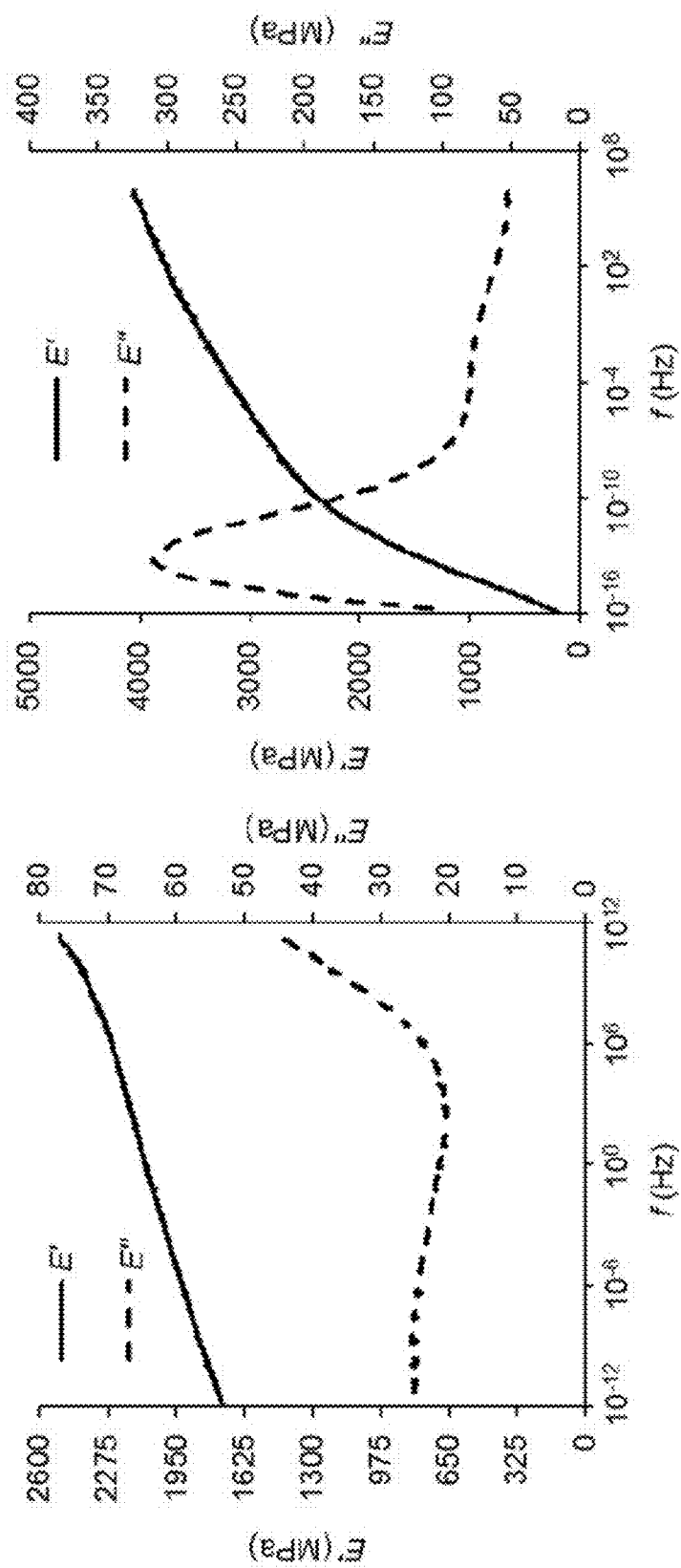
FIG. 16(a) illustrates storage and loss moduli master curves constructed using 20° C. as the reference temperature for polycarbonate.
FIG. 16(b) illustrates storage and loss moduli master curves constructed using 20° C. as the reference temperature for vinyl ester.
Figure 17:
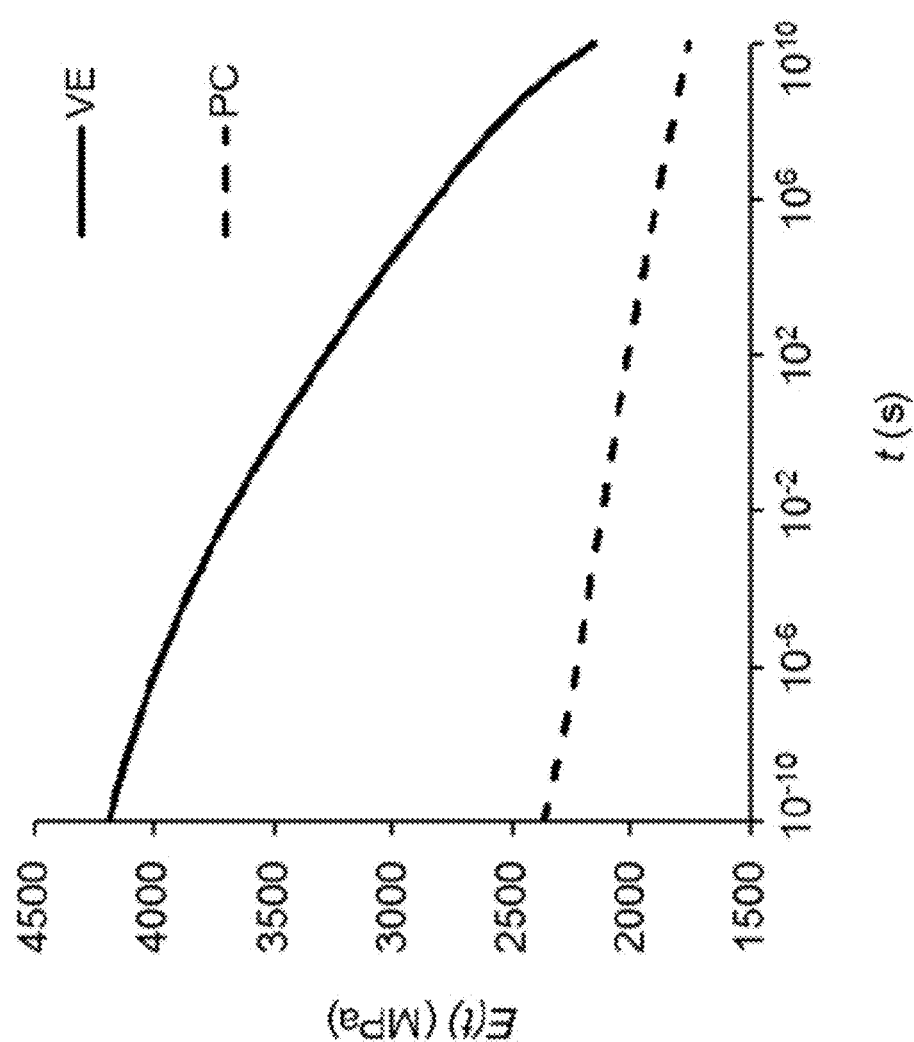
FIG. 17 illustrates time domain relaxation functions obtained for polycarbonate and vinyl ester.
Figure 18:
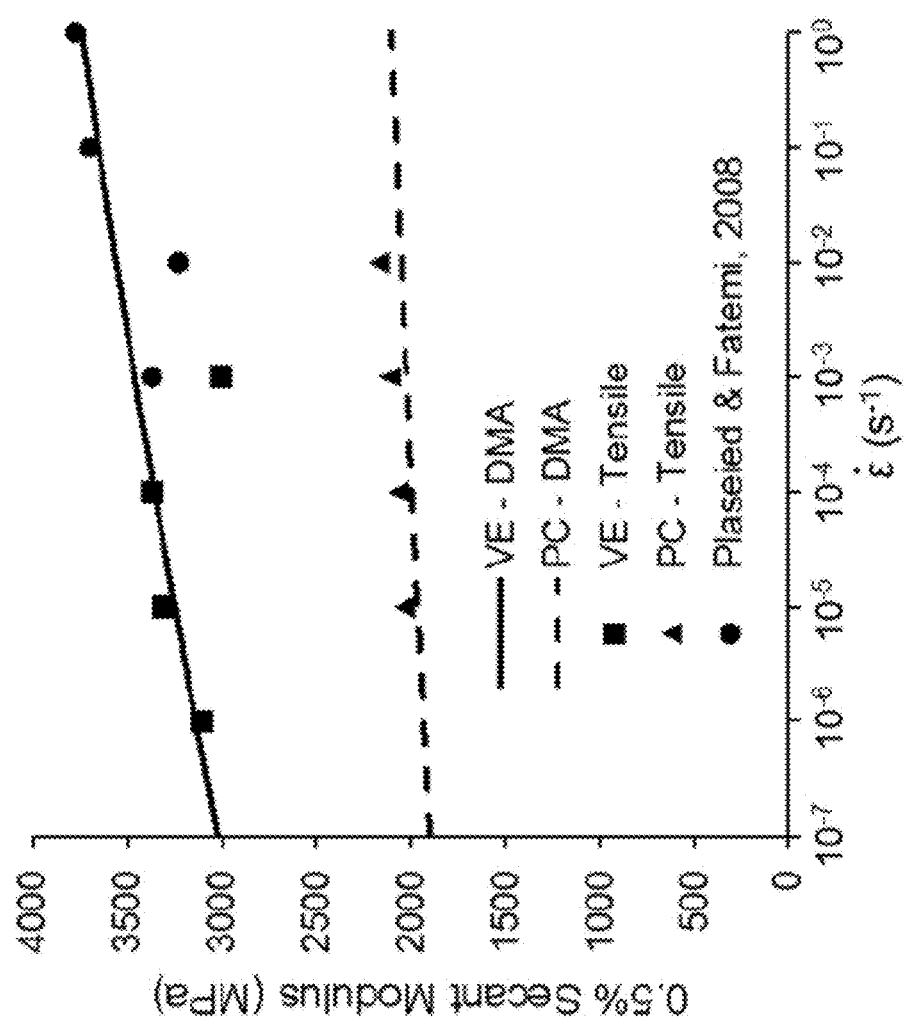
FIG. 18 illustrates a comparison of secant modulus predictions from the DMA transform for polycarbonate and vinyl ester with values from separate tensile testing and literature values.

The TTS principle was applied, as described above, to form a master curve shown in FIG. 16(B). In the VE master curve, two peaks were captured. The frequency master curve was then converted into a time domain relaxation function E(t) using the equations described above. The $R^2$ value of the curve fit to the master curve is above 0.99, indicating an appropriate fit. The zero-frequency asymptote is around −600 MPa, which violates the non-negativity condition. However, the crossover to negative storage modulus occurs at around 3×10$^{-18}$ Hz, which is sufficiently small that it has insignificant impact on the computation of E(t). From the stress-strain curve that results, various properties of interest can be calculated. The Young's modulus (elastic modulus) was estimated by evaluating the second modulus at 0.5% strain, since the elastic region for viscoelastic materials is usually not linear. The predictions of the secant modulus were compared with tensile experiments, which agreed well with the prediction (i.e., the predictions were within ±10% of the values measured in the tensile experiments). The upper limit on the strain rate for which the Young's modulus obtained from tensile tests can be matched with the predictions obtained from transforming the DMA data from frequency-domain to time-domain data was $10^9$ s$^{-1}$.

FIG. 20 illustrates the time domain relaxation functions obtained for both the PC and VE samples. FIG. 21 illustrates the comparison of secant modulus predictions from transforming the DMA data for the PC and VE samples with values from separate tensile testing and literature values.

In summary, a correlation is explored between the elastic properties and the dynamic mechanical properties of polymers. Using the time temperature superposition principle, the storage modulus is obtained for over 20 decades of frequency. A physically-motivated fitting function is used to extrapolate the storage modulus so that an integral transform can be computed, which converts the data to a time domain function. The time domain function is validated on polycarbonate (a thermoplastic polymer) and vinyl ester (a thermoset) by comparing with the results of separate tensile tests, and excellent agreement is observed over a wide range of strain rates. The relaxation function can be used in finite element simulations to determine the response to complex loading scenarios, such as the nonsteady pulse used in many high strain rate methods, or for complex geometry.

The strain rate sensitivity of materials determined in the examples above may be used to improve the design of polymeric parts in engineering designs, for example, in automotive and aerospace structures. As explained in the examples above, according to Applicant's method, a mechanical response of polymers at different temperatures and strain rates may be determined by converting frequency-domain dynamic mechanical analysis (DMA) data to the time domain. The modulus of elasticity (known from literature or separate tensile tests) as a function of the applied strain rate is compared to predictions from the DMA data transformation method described above. Close agreement between the results obtained from the two techniques is observed over the studied range of strain rates. The transformation method only relies on the assumptions of the linear theory of viscoelasticity and is expected to be applicable to a wide range of polymers and polymer-matrix composites.

Figure 6:
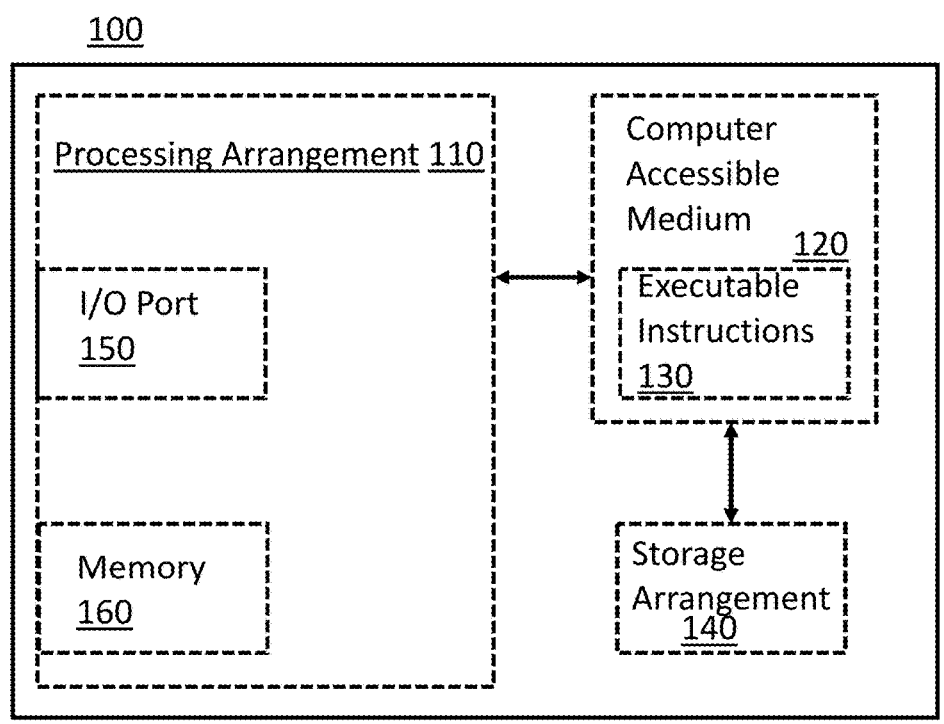
FIG. 6 illustrates a computer system for use with certain implementations.

As shown in FIG. 6, e.g., a computer-accessible medium 120 (e.g., as described herein, a storage device such as a hard disk, floppy disk, memory stick, CD-ROM, RAM, ROM, etc., or a collection thereof) may be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 may be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed:

1. A method for predicting elastic modulus of a material, the method comprising:
    providing a sample in a dynamic mechanical analysis device;
    performing a temperature sweep test including the steps of
        increasing a temperature of the sample from a predetermined minimum temperature to a predetermined maximum temperature while applying a cyclic force to the sample at a constant frequency;
        altering at least one of the storage modulus of the sample or the loss modulus of the sample while increasing the temperature; and measuring at least one of the storage modulus of the sample or the loss modulus of the sample to obtain a first data set;

performing a frequency sweep test including the steps of
increasing the temperature of the sample from a second predetermined minimum temperature to a second predetermined maximum temperature in predetermined temperature increments;

at each of the predetermined temperature increments, applying a cyclic force to the sample having a frequency that varies from a predetermined minimum frequency to a predetermined maximum frequency;

altering at least one of the storage modulus of the sample or the loss modulus of the sample while increasing the frequency of the cyclic force applied to the sample; and measuring at least one of the storage modulus of the sample or the loss modulus of the sample at discrete frequencies spaced between the predetermined minimum frequency and the predetermined maximum frequency at each of the predetermined temperature increments to obtain a second data set;

using the second data set to generate a master curve in a frequency domain of the at least one of the storage modulus of the sample or the loss modulus of the sample using time-temperature superposition;

converting the master curve in the frequency domain into a time domain relaxation function; and using the time domain relaxation function to predict the elastic modulus of the material.

2. The method of claim 1, wherein the sample comprises a polymer or a polymer composite.

3. The method of claim 1, wherein the sample comprises high density polyethylene.

4. The method of claim 3, wherein in the temperature sweep test, the predetermined minimum temperature is 35° C., the predetermined maximum temperature is 130° C., the temperature of the sample is increased at a rate of 1° C. per minute and the constant frequency is 1 Hz.

5. The method of claim 3, wherein in the frequency sweep test
the predetermined minimum frequency is 1 Hz and the predetermined maximum frequency is 100 Hz, and
at least one of the storage modulus of the sample or the loss modulus of the sample is measured at twenty discrete frequencies logarithmically spaced between 1 Hz and 100 Hz at each of the predetermined temperature increments.

6. The method of claim 1, wherein the sample comprises a syntactic foam.

7. The method of claim 6, wherein in the temperature sweep test, the predetermined minimum temperature is −100° C., the predetermined maximum temperature is 130° C., the temperature of the sample is increased at a rate of 1° C. per minute and the constant frequency is 1 Hz.

8. The method of claim 6, wherein in the frequency sweep test
the predetermined minimum frequency is 1 Hz and the predetermined maximum frequency is 100 Hz, and
at least one of the storage modulus of the sample or the loss modulus of the sample is measured at twenty discrete frequencies logarithmically spaced between 1 Hz and 100 Hz at each of the predetermined temperature increments.

9. The method of claim 1, wherein the sample comprises vinyl ester.

10. The method of claim 9, wherein in the temperature sweep test, the predetermined minimum temperature is −100° C., the predetermined maximum temperature is 170° C., the temperature of the sample is increased at a rate of 2° C. per minute and the constant frequency is 1 Hz.

11. The method of claim 9, wherein in the frequency sweep test
the predetermined minimum frequency is 1 Hz and the predetermined maximum frequency is 100 Hz, and
at least one of the storage modulus of the sample or the loss modulus of the sample is measured at twenty discrete frequencies logarithmically spaced between 1 Hz and 100 Hz at each of the predetermined temperature increments.

12. The method of claim 1, wherein the sample comprises polycarbonate.

13. The method of claim 12, wherein in the temperature sweep test, the predetermined minimum temperature is −100° C., the predetermined maximum temperature is 150° C., the temperature of the sample is increased at a rate of 1° C. per minute and the constant frequency is 1 Hz.

14. The method of claim 12, wherein in the frequency sweep test
the predetermined minimum frequency is 1 Hz and the predetermined maximum frequency is 100 Hz, and
at least one of the storage modulus of the sample or the loss modulus of the sample is measured at twenty discrete frequencies logarithmically spaced between 1 Hz and 100 Hz at each of the predetermined temperature increments.

15. The method of claim 1, wherein
generating the master curve using time-temperature superposition comprises applying a frequency shift factor to the first data set and the second data set, and
the frequency shift factor is determined according to the Williams-Landel-Ferry (WLF) equation below:

$$\log_{10} a_T = \frac{-C_1(T - T_0)}{C_2 + T - T_0} \quad (1)$$

where $a_T$ is the frequency shift factor, $C_1$ and $C_2$ are WLF coefficients, T is a temperature at which each data set is acquired, and $T_0$ is a reference temperature.

16. The method of claim 1, wherein
the master curve in the frequency domain represents the storage modulus E' at a reference temperature over a range of frequencies, and
the master curve in the frequency domain is converted into a time domain relaxation function (E(t)) using the following equation:

$$(t) = \frac{2}{\pi} \int_0^\infty \frac{E'(\omega)}{\omega} \sin(\omega t) d\omega.$$

17. The method of claim 1, wherein
the master curve in the frequency domain represents the storage modulus E' at a reference temperature over a range of frequencies, and
to extrapolate data in the frequency domain, the master curve is fitted to a sigmoidal function of log(ω) of the form:

$$E'(\omega) = a \tan h(b(\log(\omega) + c)) + d \quad (3a)$$

at a predetermined temperature, where a, b, c, and d are fit coefficients and log(w) is the natural logarithm.

18. The method of claim 1, wherein the time domain relaxation function determines a stress history generated by a specified strain history when convolved with a strain history function.

19. The method of claim 18, wherein the strain history function is of the form:

$$\sigma(t) = E \times d\varepsilon = \int_{-\infty}^{t} E(t-\tau)\frac{d\varepsilon(\tau)}{d\tau}d\tau$$

where σ, ε and τ represent stress, strain and time variable used for integration, respectively.

20. A method for predicting elastic modulus of a material, the method comprising:
   providing a sample in a dynamic mechanical analysis device;
   performing a frequency sweep test including the steps of
      increasing the temperature of the sample from a predetermined minimum temperature to a predetermined maximum temperature in predetermined temperature increments;
      at each of the predetermined temperature increments, applying a cyclic force to the sample having a frequency that varies from a predetermined minimum frequency to a predetermined maximum frequency;
      altering at least one of a storage modulus of the sample or a loss modulus of the sample while increasing the frequency of the cyclic force applied to the sample; and
      measuring at least one of the storage modulus of the sample or the loss modulus of the sample at discrete frequencies spaced between the predetermined minimum frequency and the predetermined maximum frequency at each of the predetermined temperature increments to obtain a data set;
   using the data set to generate a master curve in a frequency domain of the at least one of the storage modulus of the sample or the loss modulus of the sample using time-temperature superposition;
   converting the master curve in the frequency domain into a time domain relaxation function; and
   using the time domain relaxation function to predict the elastic modulus of the material.

* * * * *